United States Patent [19]

Makhoul et al.

[11] Patent Number: 5,611,335
[45] Date of Patent: Mar. 18, 1997

[54] HIGH-FREQUENCY FAN VENTILATOR

[76] Inventors: Imad R. Makhoul, P.O. Box 201, Judieda Village, Israel, 25110; Saleem N. Geriys, P.O. Box 113, Kfar-Yasif, Israel, 24908

[21] Appl. No.: 471,246

[22] Filed: Jun. 6, 1995

[51] Int. Cl.$^6$ ............................................. A61M 16/00
[52] U.S. Cl. .................. 128/204.24; 128/204.18; 128/204.21; 128/205.12; 128/205.15; 128/911
[58] Field of Search ................. 128/200.21, 202.13, 128/203.16, 203.24, 204.13, 204.14, 204.18, 204.24, 205.19, 204.21, 204.22, 204.25, 205.23, 911

[56] References Cited

U.S. PATENT DOCUMENTS

| | | | |
|---|---|---|---|
| 2,918,917 | 12/1959 | Emerson | 128/204.21 |
| 4,351,329 | 9/1982 | Ellestad et al. | 128/204.21 |
| 4,409,977 | 10/1983 | Bisera et al. | 128/205.15 |
| 4,440,176 | 4/1984 | Miodownik | 128/204.21 |
| 4,589,409 | 5/1986 | Chatburn et al. | 128/203.26 |
| 4,592,349 | 6/1986 | Bird | 128/204.25 |
| 4,612,929 | 9/1986 | Schübert et al. | 128/204.25 |
| 4,632,107 | 12/1986 | Butler | 128/204.24 |
| 4,681,100 | 7/1987 | Brychat et al. | 128/204.25 |
| 4,702,678 | 10/1987 | Phuc | 417/360 |
| 4,719,910 | 1/1988 | Jensen | 128/204.21 |
| 4,747,402 | 5/1988 | Reese et al. | 128/204.21 |
| 4,747,403 | 5/1988 | Gluck et al. | 128/204.21 |
| 4,770,165 | 9/1988 | Hayek | 128/202.12 |
| 4,788,974 | 12/1988 | Phuc | 128/204.21 |
| 4,805,612 | 2/1989 | Jensen | 128/204.21 |
| 4,821,709 | 4/1989 | Jensen | 128/204.21 |
| 4,838,259 | 6/1989 | Gluck et al. | 128/201.21 |
| 5,007,042 | 4/1991 | Bird | 128/200.14 |
| 5,072,726 | 12/1991 | Mazloomdoost et al. | 128/200.14 |
| 5,092,326 | 3/1992 | Winn et al. | 128/205.13 |
| 5,116,088 | 5/1992 | Bird | 285/319 |
| 5,165,398 | 11/1992 | Bird | 128/204.25 |
| 5,239,994 | 8/1993 | Atkins | 128/204.18 |
| 5,271,388 | 12/1993 | Whitam et al. | 128/204.18 |
| 5,307,794 | 5/1994 | Rauterkus et al. | 128/204.18 |
| 5,322,057 | 6/1994 | Raabe et al. | 128/204.21 |
| 5,507,282 | 4/1996 | Younes | 128/205.19 |

*Primary Examiner*—Aaron J. Lewis
*Assistant Examiner*—V. Srivastava
*Attorney, Agent, or Firm*—Merchant, Gould, Smith, Edell, Welter & Schmidt, P.A.

[57] ABSTRACT

A high-frequency fan ventilator having a rotating fan fixed via its central shaft to the base of a ventilator chamber. The chamber has separate openings for incoming pressurized air/oxygen and other openings for expelling exhaled gas rich with carbon dioxide originating from the lungs. Using the high-frequency fan ventilator, gas exchange between the lungs and the atmosphere is achieved by rotation of the fan. This rotation creates a negative pressure zone around the fan's center and leads to helical gas waves moving towards the fan's center (away from the lungs), simulating expiration of gas from the lungs. The rotation of the fan's arms also produces helical gas waves directed from the fan, to the periphery of the chamber and towards the lungs through the connector of the ventilation chamber and the endotracheal tube, which is inserted into the trachea, simulating inspiration of gas into the lungs. Adequate lung inflation is maintained by keeping a pre-set level of positive pressure within the system achieved by intermittent obstruction of the exhalation openings in the ventilation chamber's wall. Monitoring devices are coupled to the chamber to monitor and measure the temperature, humidity and pressure within the chamber.

38 Claims, 3 Drawing Sheets

HIGH-FREQUENCY FAN VENTILATOR

BACKGROUND OF THE INVENTION

1. Field of the Invention

The present invention relates in general to mechanical ventilation, and more specifically to a high-frequency fan ventilators for the treatment of respiratory failure.

2. Description of Related Art

As a result of respiratory failure, it occasionally becomes difficult for particular individuals to breathe without assistance of a respirator or other mechanical apparatus which tends to achieve adequate gas exchange between the blood/lungs and the atmosphere.

A variety of respirators are used to ventilate patients mechanically. Conventional ventilators are operated on a rate of 1–120 cycles/minute (breaths per minute). Such conventional respirators often cause trauma to the airways and to the lungs due to high volume and pressure delivered, and may often fail to provide adequate gas exchange.

To try to solve this problem, methods for high-frequency ventilation have been developed, which use less than physiologic tidal volumes in conjunction with high respiratory rates of 2–30 Hz (120–1,800 rounds or cycles per minute). Several methods and devices for the delivery of high-frequency ventilation have been patented and some of them are used clinically for the ventilation of patients, but with limited success.

U.S. Pat. No. 4,409,977 issued to Bisera, et al, herein incorporated by reference, describes a pump chamber system for high-frequency ventilation operated by a high-frequency inflating/deflating bag located within a closed chamber, thereby defining a pressure compartment between the bag and the chamber's wall. The bag is intermittently compressed by less than 10% of its volume and thus conveys pressure changes into the respiratory system of a patient.

U.S. Pat. No. 5,092,326 issued to Winn, et al, herein incorporated by reference, describes a method for high-frequency oscillatory ventilation using an oscillatory member for back and forth movement, driven by a piston and a cylinder combination, which also control the frequency and amplitude of the oscillatory member.

U.S. Pat. No. 4,838,259 issued to Clark, et al, herein incorporated by reference, describes a multi-frequency jet ventilator and method using a multi-voltage control of solenoid closed valve which helps in periodic interruption of gas flow, thus generating ventilatory pulses.

U.S. Pat. No. 4,351,329 issued to Ellestad, et al, herein incorporated by reference, describes a method for high-frequency breath pump which uses two different selected volumes driven with synchronism of inhalation and exhalation alternatively forcing gas during inspiratory phase and drawing gas during a corresponding expiratory phase.

U.S. Pat. No. 5,165,398 issued to Bird, and which is herein incorporated by reference, describes a high-frequency ventilator using a diaphragm which is associated with a serving chamber and a percussion chamber leading to high-frequency repositioning of the diaphragm from one direction to the center, and then to the other direction.

U.S. Pat. No. 4,788,974 issued to Phuc, and which is herein incorporated by reference, describes a high-frequency artificial respirator using an oscillation generation means connected to patient circuit for imparting high-frequency oscillation, and means for low-pass filtering slowly varying gas components and means for positive pressure generation being interfaced and communicating with means of low-pass filtering.

U.S. Pat. No. 5,271,388 issued to Whitwam et al, describes a ventilator which has a ventilating duct with one end attached to a patient's tube, a gas supply jet extending into the ventilator duct which is rotated about an axis by a motor at a speed corresponding to the required breathing rate, thus producing cyclical flow of gas to and from the patient. However, Whitwam et al uses jet pulses rotated about an axis, rather than a rotating fan or fan's arms.

Thus, it can be seen that high-frequency ventilation modes which have previously been used differ clinically in the following characteristics: (1) frequency of ventilation; (2) ventilatory impulse generation (jet, flow interruption, oscillation); (3) need for conventional ventilatory pressure back-up; (4) port of entry of the ventilatory impulse into the airway; (5) pressure monitoring ports in the ventilation circuit; and (6) pattern of expiration: active or passive.

The main rationale for the use of high-frequency ventilation modes is to minimize barotrauma to lungs and airways caused by high inflation volumes and/or pressures used in conventional respirators, and to try to achieve better gas exchange and alleviate respiratory failure. Therefore, high-frequency ventilation modes use small tidal volumes (equal or less than the dead space volume) with higher than physiological respiratory rates. High-frequency jet ventilation and high-frequency flow interruption have been proven to be effective in treating pulmonary interstitial emphysema, while the use of high-frequency oscillatory ventilation in neonates reduces both the need for extracorporeal membrane oxygenation (ECMO) and to some extent the risk for development of long-term chronic lung disease. However, the above-mentioned three modes do not significantly reduce mortality from respiratory failure.

In addition, the anticipated change in gas exchange and ventilation with the above mentioned high-frequency ventilation modes is questionable, slowly achieved (within hours), and is accompanied by side effects. Those side effects include humidification problems, injury to airway mucosa with life-threatening airway obstruction, systemic air emboli and reduction of venous return to the heart, thus comprising its function and causing hypotension and heart failure. In addition, high-frequency jet ventilation, high-frequency oscillatory ventilation, and high-frequency flow interruption are relatively difficult to handle and very expensive.

Fans have not been used previously for therapeutic mechanical ventilation in humans or animals. While one study used a ventilation fan on a research basis, ventilation fans have not been used for ventilation and gas exchange (Upton CJ, Milner AD, Stokes GM, Carman PGT, "What are the mechanisms producing increased ventilation in dead space studies in neonates?" *Pediatr Pulmonol* 1990; 9: 136–139.) In this study, hereby incorporated by reference, the effect of adding external dead space tube on minute ventilation and on end-tidal oxygen and carbon dioxide tensions in ventilated infants was examined. The additional tube produced a significant rise in minute ventilation, an effect which was decreased, but not abolished, by the use of a ventilation fan inside the additional tubing.

Furthermore, fans have been widely used to ventilate closed areas at homes, factories or offices and thus lead to exchange of gas. Fans can either ventilate a specific area by forward helical waves (positive pressure) or by backward helical waves (negative pressure), thus sucking gas from a particular area (vacuum). The above characteristics are observed as long as both sides of the fan (in front and behind the fan's arms) are free and not obstructed.

It can be seen then that there is a need for a high-frequency fan ventilator which delivers helical rotatory waves.

It can also be seen that there is a need for a fan ventilator wherein the rotation of the fan causes two distinct types of helical rotating waves for simulating expiration of gas from the lungs while also simulating an active inspiration of gas into the lungs.

It can also be seen that there is a need for a fan ventilator system which includes measurement and monitoring of humidification, temperature and pressure.

Another aspect of the present invention is that an appropriate oxygen mixture is rapidly delivered to the lungs.

It can also be seen that there is a need for a fan ventilator system which avoids causing barotrauma to airway and lungs caused by high ventilatory pressures.

SUMMARY OF THE INVENTION

To overcome the limitations in the prior art described above, and to overcome other limitations that will become apparent upon reading and understanding the present specification, the present invention discloses a new high-frequency fan ventilator. The high-frequency fan ventilator delivers helical rotatory waves, in contrast to other modes of ventilation which deliver either high-volume positive bulk waves (as in conventional mechanical ventilation) or small-volume forward waves (high-frequency jet ventilation, high-frequency flow interruption), or small forward/backward waves (as in high-frequency oscillatory ventilation).

One side of the fan is blocked by a sealed plane or plate. The fan rotation thus causes two distinct types of helical rotating waves in a closed chamber or a ventilation tube. First, helical gas waves moving towards the center of the fan's shaft simulate an active expiration of gas from the lungs. Secondly, helical gas waves in the peripheral portion of the fan's arms moving away from the fan towards the connection to the lung, thereby simulating an active inspiration of gas to the lungs.

External blended oxygen/air, which is administered beyond the fan's arms, is rotated, mixed and pushed towards the lungs. Gas which is helically sucked towards the fan's shaft is expelled by the rotating fan's arms to the external atmosphere. The frequency of ventilation is variable (200–20,000 rounds per minute). The system also includes measurement and monitoring of humidification, temperature and pressure. A safety valve is attached to the ventilation chamber to prevent over-pressure in the system. Varying the surface area of the larger plane of the fan's arm allows selection of the amplitude of the ventilation waves.

A system in accordance with the principles of the present invention comprises a ventilation chamber having containment walls, a base and a ventilation port for directing gases to and from a patient; a fan, disposed at the base of the ventilation chamber, the fan having a shaft for holding fan arms, the shaft of the fan having a lumen through the length thereof, the lumen connecting the inside of the ventilation chamber to outside air and providing a port for exhaled gases; and a fan rotator, coupled to the fan, for rotating the fan at a selectable velocity, the rotation of the fan providing positive and negative helical waves for inspiration and expiration.

The present invention solves the above-described problems by providing a supplementary pressurized air or oxygen flow through auxiliary openings and their paths, preferably located in the wall of the ventilation chamber and gas flow directed away from fan. Additional openings in the ventilation chamber's wall expel expiratory gas (rich with carbon dioxide) from the ventilation chamber to the atmosphere. Valves control the pressure inside the ventilation chamber. Ports and hardware for monitoring pressure, temperature and humidification in the ventilatory chamber are also included.

One aspect of the present in invention is that negative and positive helical waves are generated.

Another aspect of the present invention is that the negative and positive helical waves combine with high-frequency fan ventilation to provide excellent mixing of gas in the whole chamber, endotracheal tube, airways and lungs thereby resulting in efficient gas exchange and improved oxygenation and ventilation.

Another aspect of the present invention is that hypercapnia (elevated carbon dioxide) in ventilated patients with respiratory failure is eliminated.

Another aspect of the present invention is that an appropriate oxygen mixture is rapidly delivered to the lungs.

Another aspect of the present invention is that barotrauma to airway and lungs caused by high ventilatory pressures used in conventional ventilation is avoided.

Still another apsect of the present invention is that cardiac compromise occurring with other modes of high-frequency ventilation is avoided.

Another aspect of the present invention is that the ventilator is less expensive than other modes of high-frequency ventilation and provides simplicity of handling, maintenance and operation.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there is illustrated and described specific examples of an apparatus in accordance with the invention.

BRIEF DESCRIPTION OF THE DRAWINGS

Referring now to the drawings in which like reference numbers represent corresponding parts throughout.

DETAILED DESCRIPTION OF THE INVENTION

In the following description of the preferred embodiment, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

The present invention provides a high frequency fan ventilator 10 according to the present invention. Oxygenation is improved by increases in either the fraction of oxygen in inspired gas ($FiO_2$) and/or by increasing the mean airway pressure ($P_{aw}$) which is also affected by the rate of gas flow entering the system. Increases in frequency and/or ventilation amplitude may also improve oxygenation, but to a lesser extent. Ventilation (carbon dioxide removal) is mainly controlled by either the frequency of the fan's rotation, the mean airway pressure, and/or the amplitude of ventilation waves (which is mainly determined by the area of the larger surface of the fan's arms).

Figure 1:
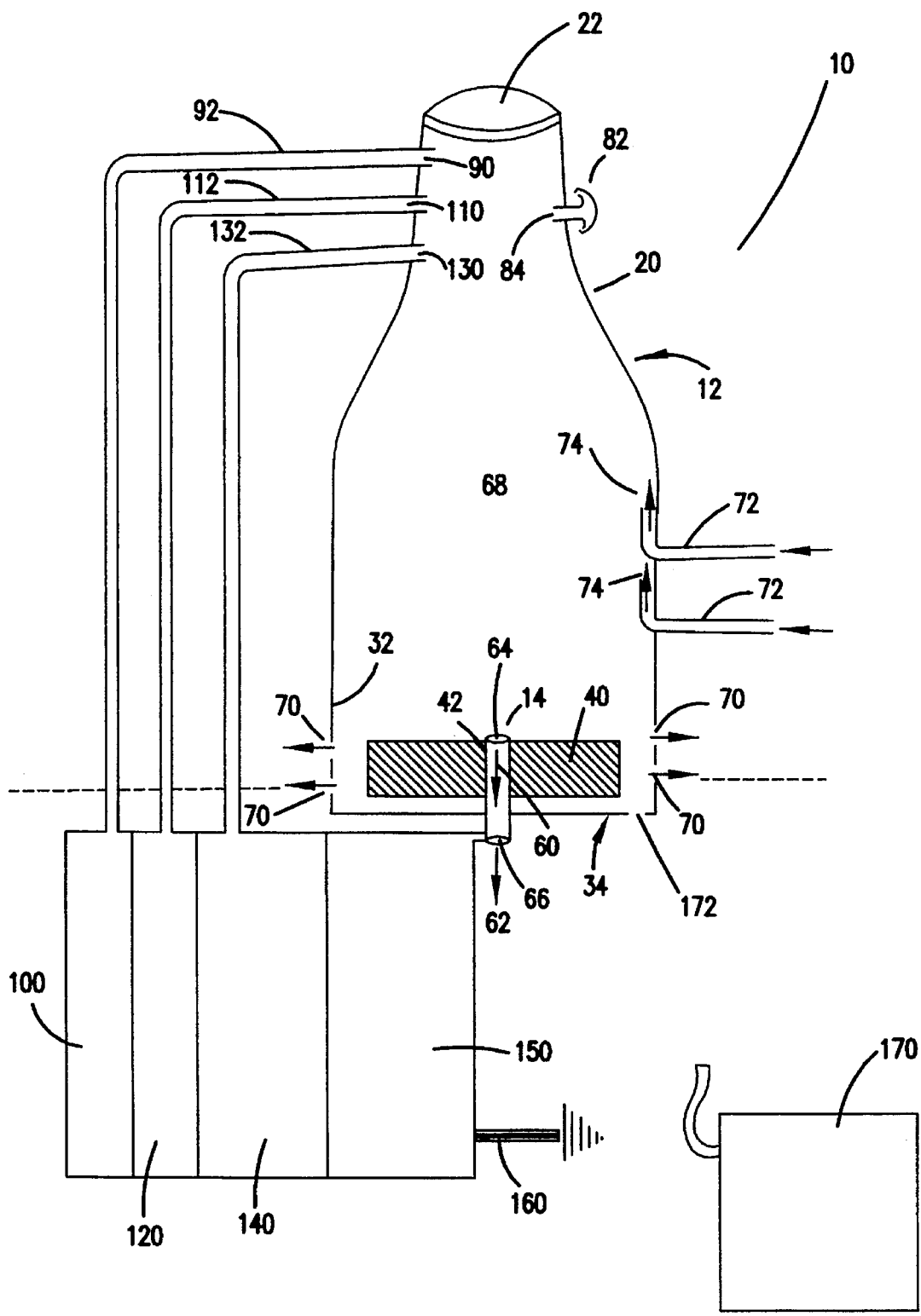
FIG. 1 is a side cross-sectional view of the high-frequency fan ventilator of the present invention.

Referring to FIG. 1, the chamber 12 serves for gas flow both in the direction to and away from the fan 14. The chamber's 12 shape is tridimentional and may be cylindrical, rectangular box, conic or cubic. The volume of the chamber 12 is preferably 500–15,000 ml. The chamber 12 has a tapering or narrowing neck 20 which is connected eventually to the patient's endotracheal tube at connector or ventilation port 22. At the center of the chamber's base 34, the rotating fan 14 is fixed. The wall 32 of chamber 12 preferably has a thickness of 1–5 mm. The base 34 of the chamber 12 serves for obstructing gas flow from the fan 14 in the direction of the base 34 (contrary to regular ventilation fans in rooms or offices), and has the rotating fan 14 fixed to it.

The arms 40 of the fan 14 are connected to a fan shaft 42. The shape of each arm 40 may be square, rectangular, triangular or ellipsoid; but in the preferred embodiment is rectangular. The angle between the larger plane (length & width) of the fan's arm 40 and the chamber's base 34 is preferably 90 degrees, i.e., the planes formed by fan's arms 40 are perpendicular to the chamber's base 34. However, this angle can be varied. For example, angles between +35 and +150 degrees are effective but yet not as efficient. In the preferred embodiment, each arm may be 2–50 cm in length, 0.5–20 cm wide, and 0.5–10 mm thick. The velocity of fan 14 is variable with 200–20,000 rpms preferred. However, it is to be understood that this velocity may be changed as needed.

The shaft 42 of the fan has a cylindrical or rectangular box shape. Preferably the shaft 42 has an internal radius of 2–15 mm, a height of 1–20 cm, and a thickness of the wall of 1–5 mm. The shaft 42 has a cylindrical or rectangular box lumen 60 through its whole length. This lumen 60 connects the inside of the chamber 12 to the atmosphere 62. This lumen 60 may be open or closed as medically necessary. The internal opening 64 of the fan's shaft 42 may be circular, square or rectangular. Preferably the shaft internal opening 64 has a radius of 2–15 mm, and a thickness of the wall of 1–5 mm. The external opening 66 of fan's shaft 42 could be circular, square or rectangular. Preferably, the external opening 66 of the fan's shaft 42 has a radius of 2–15 mm, and a thickness of the wall of 1–5 mm.

The openings 70, through the container's wall 32 serve for movement of gas from inside the chamber 12 to outside the chamber 12. The openings 70 are preferably located close to the fan's arms 40, but could be located at any point on the walls 32 of the chamber 12. Preferably, there are several openings 70 spaced about the container 12, with each opening generally having a width or diameter of 2–40 mm. Each opening 70 could be intermittently closed or obstructed partially or fully, at a rate of 1–120/minute, as a pneumatic valve, or as a valve controlled by a microprocessor and a computer in order to create and maintain a positive pressure of 0–40 cm $H_2O$ in the chamber 12 (and consequently in the respiratory system) as pre-set clinically to sustain lung inflation.

Internal paths 72 introduce the gas which is enriched with pressurized air and or oxygen into the chamber 12. The oxygen ports 74 and the internal paths 72 extend through the chamber's wall 32, preferably not close to the fan's arms 40. Nevertheless, it is to be understood that the oxygen ports 74 and internal paths 72 could be located at any point on the walls 32 of the chamber 12. The paths 72 are shaped in such a way so that the direction of entering gas is towards the ventilation port 22 of the chamber 12, in opposition to the direction of the fan 40 location.

Ventilation port 22 in chamber 12 connects the chamber 12 to the patient's endotracheal ventilation tube which leads to the patient's lungs. The ventilation port 22 may be circular and preferably has an internal radius of 10–30 mm. Additional tubing may be needed between the ventilation port 22 and the patient's endotracheal tube.

Pop-off valve 82 functions as a safety valve. If the pressure inside the chamber 12 exceeds a pre-set pressure of 20–80 cm $H_2O$, then this valve 82 opens immediately and releases extra pressure from the system 10. The internal opening 84 of the safety valve 82 is located in the wall 32 of the chamber 12. The safety valve opening 84 may be configured with a circular, rectangular or square shape and preferably has a radius or length of 2–20 mm.

Temperature monitoring port 90 facilitates the measurement and continuous monitoring of the temperature inside the chamber 12. The temperature monitoring port 90 has a shape that is circular or square, and has a radius or length of 2–15 mm. Furthermore, the temperature monitoring port 90 is located in the wall 32 of chamber 12 close to the ventilation port. Temperature monitoring tube 92 connects the temperature monitoring port 90 to device 100 which continuously measures, monitors and displays temperature of gas inside the chamber 12. Preferably the temperature of the gas inside the chamber 12 is maintained at 31°–34° C.

Pressure monitoring port 110 is for measurement and continuous monitoring of pressure inside the chamber 12. The pressure monitoring port 110 has a shape that is circular or square and has a radius or length of 2–15 mm. The pressure monitoring port 110 is also located in the wall 32 of chamber 12 close to the ventilation port 22. Pressure monitoring tube 112 connects pressure measurement port 110 to pressure monitor 120 which continuously measures, monitors and displays pressure of gas inside the container 12.

Humidity monitoring port 130 is used for the measurement and continuous monitoring of humidity inside the chamber 12. The shape of the humidity monitoring port 130 is circular or square and has a radius or length of 2–15 mm. Preferably humidity monitoring port 130 is located in the wall 32 of chamber 12 close to ventilation port 22. Humidity monitoring tube 132 connects humidity measurement port 130 to humidity monitoring devide 140 which continuously measures, monitors and displays the humidity of the gas inside the chamber 12 with the humidity preferably maintained at 40–100% as pre-set clinically.

Fan rotator 150 rotates the fan 14. The fan rotator 150 allows any velocity to be chosen in the range of 200–20,000 rmp (rounds per minute). The fan rotator 150, as well as monitoring devices 100, 120, 140 are connected to an electrical power source 160, and controlled by a computer (not shown).

A water trap 170 may be implemented with the system to drain extra water/fluid from the ventilation system 10. This water trap 170 may be connected either to the lower side of the said ventilation chamber 12 via drain 172, to the lower side of the ventilation port 22 or to the lower side of the additional tubing between the chamber and the patient's endotracheal tube (not shown).

Figure 2:
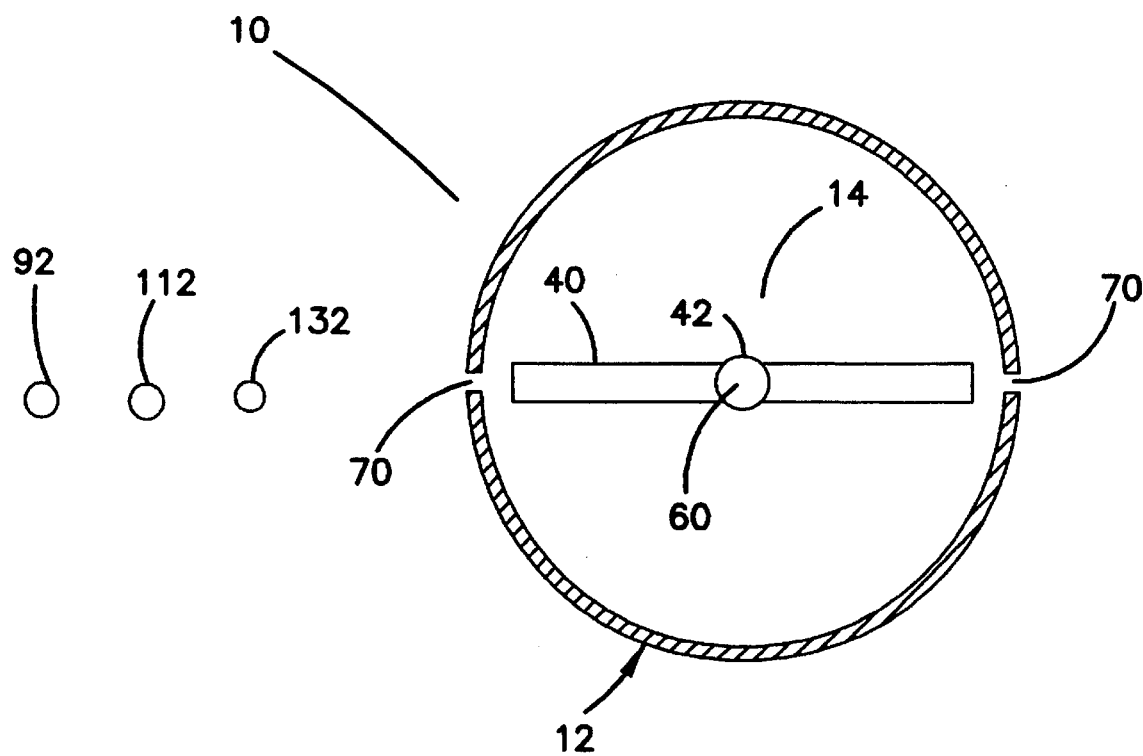
FIG. 2 is a lateral cross-sectional view of the high-frequency fan ventilator of the present invention.

FIG. 2 is a lateral cross-sectional view of the high-frequency fan ventilator 10. The fan 14 is shown disposed within the walls 32 of the chamber 12. The shaft 42 of the fan 14 supports the arms 40 of the fan 14 and a lumen 60 through the shaft 42 connects the inside of the chamber 12 to the atmosphere. This lumen 60 may be open or closed as medically indicated. Temperature monitoring 92 connects the temperature monitoring port to the temperature monitoring device (not shown in FIG. 2). Pressure monitoring tube 112 connects pressure measurement port to pressure monitor (not shown in FIG. 2). Humidity monitoring tube 132 connects humidity measurement port to humidity monitoring devide (not shown in FIG. 2).

Figure 3:
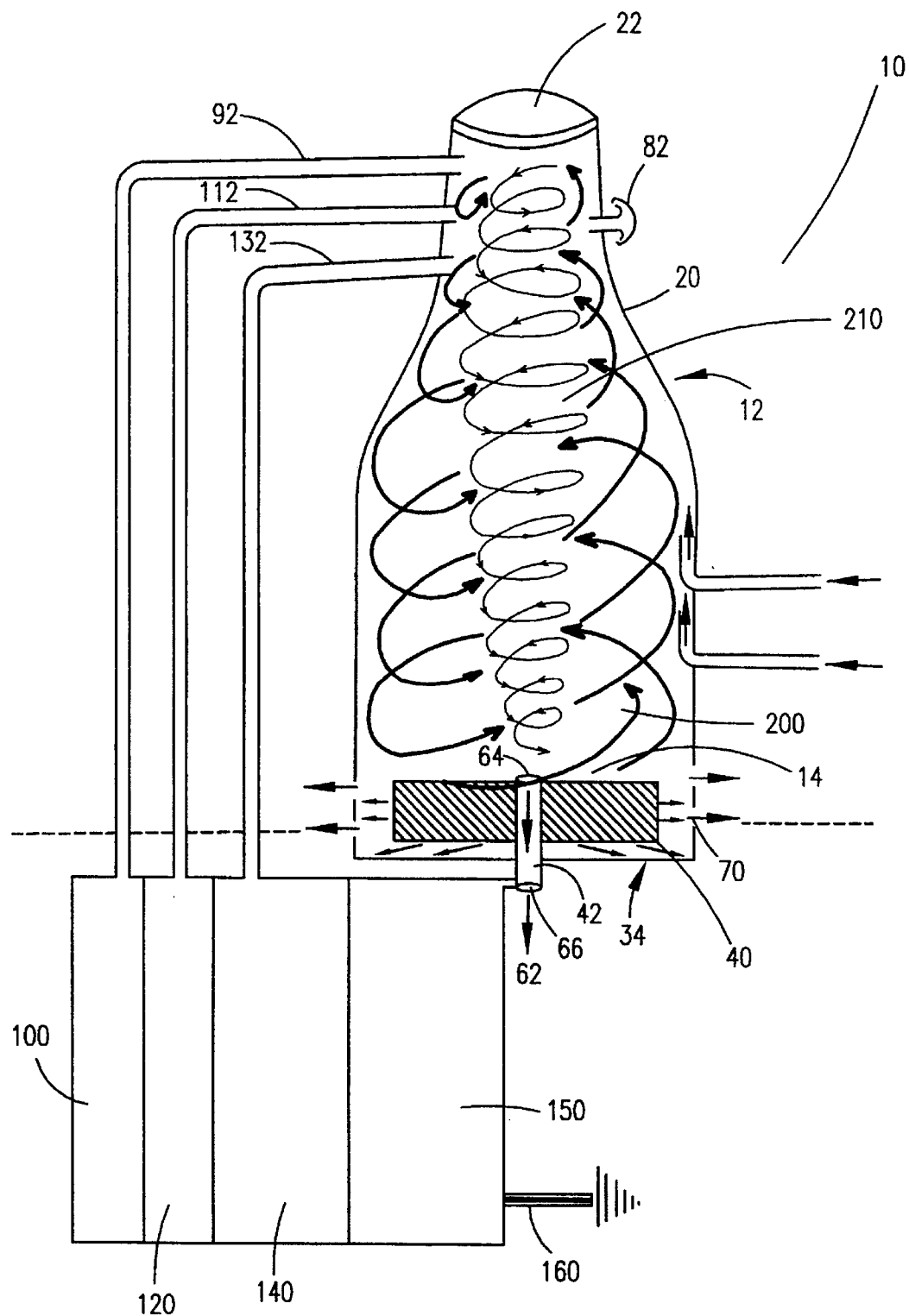
FIG. 3 is a side cross-sectional view of the high-frequency fan ventilator of the present invention showing the direction of helical gas flow during the rotation of the fan towards the rotating fan (expiration-thin line waves) and away from the fan (inspiration-thick line waves).

FIG. 3 is a side cross-sectional view of the high-frequency fan ventilator 10 of the present invention showing the direction of helical gas flow during the rotation of the fan 14. Positive helical waves 200 in the peripheral portion of the chamber 12 move away from the fan 14 towards the ventilation port 22 for active inspiration of gas to the lungs. Negative helical waves 210 move towards the center of the chamber 12 from the ventilation port 22 to the shaft 42 of the fan 14 for active expiration of gas from the lungs.

In summary, a novel high-frequency ventilator and method has been disclosed. Those skilled in the art will recognize that the present invention may be combined with other techniques known in the art such as maintaining and monitoring of pressure, humidification, and temperature inside the ventilation system, and achieving better gas exchange between the patient's lungs and the gas outside the patient and using less pressure during ventilation, thus avoiding barotrauma to airways and lungs, and the like.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather by the claims appended hereto.

What is claimed is:

1. A ventilator, comprising:
    a ventilation chamber having containment walls, a base and a ventilation port for directing gases to and from a patient;
    a fan, disposed at the base of the ventilation chamber, the fan having a shaft for holding fan arms, the shaft of the fan having a lumen through the length thereof, the lumen connecting the inside of the ventilation chamber to outside air and providing a port for exhaled gases; and
    a fan rotator, coupled to the fan, for rotating the fan at a selectable velocity, the rotation of the fan providing positive and negative helical waves for inspiration and expiration.

2. The ventilator of claim 1 wherein the positive helical waves in the peripheral portion of the chamber move away from the fan towards the ventilation port for active inspiration of gas to the lungs.

3. The ventilator of claim 1 wherein the negative helical waves move towards the center of the chamber from the ventilation port to the shaft of the fan for active expiration of gas from the lungs.

4. The ventilator of claim 1 wherein the chamber collects inspiration gases through inlet ports prior to inspiration and discharges expiration gases through exit ports after expiration.

5. The ventilator of claim 4 wherein the ventilation chamber mixes the inspiration gases prior to directing the ventilation gases out the ventilation port.

6. The ventilator of claim 1 wherein the chamber has a narrowing neck leading to the ventilation port for directing gas flow to and from the patient.

7. The ventilator of claim 1 wherein the base of the ventilation chamber having the rotating fan disposed thereto obstructs gas flow from the fan in the direction of this base.

8. The ventilator of claim 1 wherein the arms of the fan are perpendicular to the chamber's base.

9. The ventilator of claim 1 wherein the number of arms for the fan and the dimensions of each arm are chosen to produce a predetermined amplitude for the helical waves generated by the fan.

10. The ventilator of claim 1 wherein the velocity of fan is variable.

11. The ventilator of claim 1 wherein the lumen of the fan's shaft is capable of being selectably opened and closed.

12. The ventilator of claim 1 wherein the chamber further comprises a first set of apertures in the wall of the chamber for movement of gas from inside the chamber to outside the chamber to the outside air.

13. The ventilator of claim 12 wherein the size of the apertures are selectably and intermittently controlled to maintain a positive pressure in the ventilation chamber thereby sustaining lung inflation.

14. The ventilator of claim 1 wherein the chamber further comprises a second set of apertures in the wall of the chamber introducing gas enriched with pressurized air and oxygen into the ventilation chamber.

15. The ventilator of claim 1 wherein the chamber further comprises a pop-off valve which for preventing the pressure inside the ventilation chamber from exceeding a pre-set value.

16. The ventilator of claim 1 further comprising measurement and monitoring means, coupled to the chamber, for monitoring environmental characteristics inside the ventilation chamber.

17. The ventilator of claim 16 wherein the measuring and monitoring means further comprises display means for displaying the environmental characteristics inside the ventilation chamber.

18. The ventilator of claim 16 wherein the measurement and monitoring means is controlled by a computer.

19. The ventilator of claim 16 wherein the environmental characteristics monitored and measured are temperature, humidity and air pressure.

20. The ventilator of claim 1 wherein the chamber further comprises a water trap for draining fluid from the chamber.

21. A high-frequency fan ventilator, comprising:
    a ventilation chamber having containment walls, a base and a ventilation port for directing gases to and from a patient;
    a fan, disposed at the base of the ventilation chamber, the fan having a shaft for holding fan arms, the shaft of the fan having a lumen through the length thereof, the lumen connecting the inside of the ventilation chamber to outside air and providing a port for exhaled gases;
    a variable, high-speed fan rotator, coupled to the fan, for rotating the fan at a selectable velocity, the rotation of the fan providing positive and negative helical waves for inspiration and expiration; and measurement and monitoring means, coupled to the chamber, for monitoring environmental characteristics inside the ventilation chamber.

22. The ventilator of claim 1 wherein the positive helical waves in the peripheral portion of the chamber move away from the fan towards the ventilation port for active inspiration of gas to the lungs.

23. The ventilator of claim 1 wherein the negative helical waves move towards the center of the chamber from the ventilation port to the shaft of the fan for active expiration of gas from the lungs.

24. The ventilator of claim 21 wherein the chamber collects inspiration gases through inlet ports prior to inspiration and discharging expiration gases through a exit port after expiration.

25. The ventilator of claim 24 wherein the ventilation chamber mixes the inspiration gases prior to directing the ventilation gases out the ventilation port.

26. The ventilator of claim 21 wherein the chamber has a narrowing neck leading to the ventilation port for directing gas flow to and from the patient.

27. The ventilator of claim 21 wherein the base of the ventilation chamber having the rotating fan disposed thereto obstructs gas flow from the fan in the direction of this base to create the positive and negative helical waves.

28. The ventilator of claim 21 wherein the arms of the fan are perpendicular to the chamber's base.

29. The ventilator of claim 21 wherein the number of arms for the fan and the dimensions of each arm are chosen to produce a predetermined amplitude for the helical waves generated by the fan.

30. The ventilator of claim 21 wherein the lumen is capable of being selectably opened and closed.

31. The ventilator of claim 21 wherein the chamber further comprises a first set of apertures in the wall of the chamber for movement of gas from inside the chamber to outside the chamber to the outside air.

32. The ventilator of claim 31 wherein the size of the apertures are selectably and intermittently controlled to maintain a positive pressure in the ventilation chamber thereby sustaining lung inflation.

33. The ventilator of claim 21 wherein the chamber further comprises a second set of apertures in the wall of the chamber introducing gas enriched with pressurized air and oxygen into the ventilation chamber.

34. The ventilator of claim 21 wherein the chamber further comprises a pop-off valve which for preventing the pressure inside the ventilation chamber from exceeding a pre-set value.

35. The ventilator of claim 21 wherein the measureing and monitoring means further comprises display means for displaying the environmental characteristics inside the ventilation chamber.

36. The ventilator of claim 21 wherein the measurement and monitoring means is controlled by a computer.

37. The ventilator of claim 21 wherein the environmental characteristics monitored and measured are temperature, humidity and air pressure.

38. The ventilator of claim 21 wherein the chamber further comprises a water trap for draining fluid from the chamber.

* * * * *

UNITED STATES PATENT AND TRADEMARK OFFICE
CERTIFICATE OF CORRECTION

PATENT NO. : 5,611,335

DATED : Mar. 18, 1997

INVENTOR(S) : Makhoul et al.

It is certified that error appears in the above-identified patent and that said Letters Patent is hereby corrected as shown below:

On title page, in [56], "Whitam" should read --Whitwam--.

In column 1, line 8, "ventilators" should read --ventilator--.

In column 4, line 10, delete "in" after "present".

In column 5, line 16, "tridimentional" should read --tridimensional--.

In column 6, line 56, "devide" should read --device--.

In column 7, line 18, "devide" should read --device--.

In column 8, line 37, claim 15, insert --is-- after "which".

In column 9, line 14, claim 24, "a exit" should read --an exit--.

In column 10, line 16, claim 34, insert --is-- after "which"; line 19, claim 35 "measureing" should read --measuring--.

Signed and Sealed this

Second Day of December, 1997

*Attest:*

BRUCE LEHMAN

*Attesting Officer*      *Commissioner of Patents and Trademarks*